US00PP08099P

United States Patent [19]

Mojonnier

[11] Patent Number: Plant 8,099

[45] Date of Patent: Jan. 12, 1993

[54] ALSTROEMERIA PLANT NAMED LORENA

[76] Inventor: Erwin Mojonnier, 237 Quail Dr., Encinitas, Calif. 92024

[21] Appl. No.: 720,684

[22] Filed: Jun. 25, 1991

[51] Int. Cl.[5] ..... A01H 5/00
[52] U.S. Cl. ..... Plt./87.1
[58] Field of Search ..... Plt./87.1

*Primary Examiner*—James R. Feyrer
*Attorney, Agent, or Firm*—Foley & Lardner

[57] ABSTRACT

A distinct cultivar of Alstroemeria plant named Lorena, particularly characterized by its low maintenance; early December flowering through photoperiodic control, good post-harvest color retention, and by its flowers which have dark pink cheeks with a white background, dark purple streaking on the upper and lower petals and along the edges of the sepals, and patches of yellow on the two upper plates.

1 Drawing Sheet

The present invention relates to a new and distinct cultivar of Alstroemeria plant hereinafter referred to by the cultivar name Lorena.

Lorena is a product of a planned breeding program which had the primary objectives of creating new Alstroemeria cultivars having unique flower color and being capable of early winter production with low maintenance requirements. The latter term refers to the production of a minimum of non-flowering stems.

In order to fully understand an important characteristic of the new cultivar, an explanation of typical current winter production schedules for cut flowers of Alstroemerias would be helpful. Standard industry growing practices normally utilize only natural daylight. As a result, late fall and winter production of Alstroemeria cut flowers, due to reduced levels of light during these periods, typically requires 12 weeks or more of growing time from the planting of the rhizome cutting to the initiation of flowering. Even more time is required for further flowering to produce a stem ready for sale. With certain varieties, the period of time from planting to flowering can extend up to almost six months. This time will substantially vary from variety to variety, and growing techniques and conditions also affect the growing period. For example, a larger cutting will obviously require a shorter growing time than a relatively small cutting. High temperatures normally have an adverse affect on growth, as does reduced light.

The commercial implications of relatively slow growth characteristics under natural light conditions should be obvious. Increased bench or field time (if grown outdoors where climates permit) substantially increases production costs, which in turn result in increased costs per stem due to the increased cost of production. Total production of Alstroemeria cut flowers during such period is also correspondingly less. This adversely affects the normal supply/demand ratio to the marketplace, and as a result cut flowers of Alstroemeria are substantially more costly during the winter months than during the periods beginning in March when production increases. It is not unusual for stem prices to be 50% higher during the winter months of December, January, and February.

The inventor has discovered that through photoperiodic growth practices, certain cultivars can be brought into flowering in the late fall and winter periods in substantially reduced periods of time, thereby increasing production during these periods. However, all cultivars are not adaptable to photoperiodic control.

Through extensive breeding, the inventor has been able to produce new Alstroemeria cultivars, of which Lorena is one, specifically adaptable to photoperiodic control. The inventor's preferred growing technique includes growing the newly stuck plants under natural light conditions for approximately one month without light supplement. After approximately one month, the day length is effectively increased by providing four hours of artificial lighting by techniques or methods well known in the industry.

A preferred growing regimen which has provided excellent results comprises planting established rhizome divisions in ground beds near the end of August or first of September. Beginning approximately one month after planting, and continuing to April 1, the plants are subjected to light from 2:00 a.m. to 6:00 a.m. daily. A lighting system which has proved highly effective consists of 135 watt bulbs spaced every 10 feet, and hung approximately 7 feet above the ground. The rhizome divisions are positioned in rows that are spaced 12 feet apart.

By effectively increasing the day length by means of artificial lighting, flowering can be initiated in a much shorter time. Within approximately six (6) weeks the first flower appears, and saleable steams are ready from mid-November to mid-Decemeber, depending upon the variety. In many instances, flowering is essentially continuous until June when the stems are too short to sell as cuts without heavy shading and some method of cooling. Without shading and cooling to prolong commercial stem production, it is common practice to dig up and divide the plants. The divided plants are then stuck in late August or early September as described, and the cycle repeated. It has also been noted that the increased light regimen has resulted in longer stems, a very desirable quality.

Lorena was originated by the inventor Erwin Mojonnier from a hybridization made in a controlled breeding program in Encintas, Calif. in 1988. The female parent was a cultivar identified as 305, a tall plant with a pink cheek against a white background, heavily streaked on upper and lower petals and with a yellow patch on the upper petals. The male parent was a cultivar identified as L4, a tall plant with a red flower, streaking on the upper and lower petals, and with a yellow patch on the upper petals.

Lorena was discovered and selected as one flowering plant within the progeny of the state parentage by the inventor in May, 1988 in a controlled environment in Encinitas, Calif.

The first act of asexual reproduction of Lorena was accomplished when vegetative cuttings were taken by the inventor from the initial selection in August, 1988, in a controlled environment in Encinitas, Calif. Horticultural examination of selected units initiated in 1989 has demonstrated that the combination of characteristics as herein disclosed for Lorena are firmly fixed and retained through successive generations of asexual reproduction.

Lorena has not been observed under all possible environmental conditions. The phenotype may vary significantly with variations in environment such as temperature, light intensity and day length. The following observations, measurements and comparisons describe plants grown in Encinitas, Calif. under greenhouse conditions which approximate those generally used in commercial practice.

The following traits have been repeatedly observed and are determined to be basic characteristics of Lorena, which in combination distinguish this Alstroemeria as a new and distinct cultivar:

1. Low maintenance, with a low number of non-flowering stems produced per plant.
2. Winter production beginning in December due to adaptability of cultivar to specified photoperiodic control regimens.
3. Lorean is easily propagated.
4. Possesses good post-harvest color retention.

The accompanying color photographic drawing shows in a top perspective closeup view typical inflorescence and foliage characteristics of Lorena, with colors being as nearly true as possible with illustrations of this type. As depicted in the closeup photograph, Lorena possesses a dark pink cheek, with white in the background. Prominent streaking is found on the upper and lower petals and streaking is also evident along the edges of the sepals. Yellow patches are found on the two upper petals.

In the following description, color references are made to The Royal Horticultural Society Colour Chart (R.H.S.). The color values were determined between 7:00 and 7:45 a.m. on May 11, 1990, under 100 foot candles of light intensity at Encinitas, Calif.

Classification:

*Botanical.*—Alstroemeria cv Lorena.

*Commercial.*—Alstroemeria.

PLANT

Form: Cut flower.

Height: Approximately 123 cm. at time of harvest.

Propagation: Originates from rhizome.

Foliage:

Quantity.—Approximately 23 leaves per stem.

*Size of leaf.*—Approximately 16.8 cm.×2.8 cm.

*Shape of leaf.*—Lanceolate.

*Color.*—Upper side, green 137A; under side green 137C.

Rhizomes:

*Color.*—White, 155B.

*Size.*—Approximately 1 cm.×1 cm. at growing tip.

INFLORESCENCE

Bud:

*Form.*—Indeterminate.

*Diameter.*—1.5 cm.

*Length.*—4.2 cm.

*Calyx.*—4 mm.

*Peduncle.*—2.5 cm. in length.

*Color.*—Green, 138B.

Flower:

*Size.*—6.3 cm. in diameter.

*Borne.*—3-5 flowers per umbel.

*Blooming habit.*—Early; begins flowering in December.

*Shape.*—Asymmetrical.

Color:

*Upper surface.*—Cheek red-purple 63C; Outer red-purple 63A.

*Under surface.*—Cheek red-purple 63A; Outer red-purple 63C.

*Other notations.*—Streaking approximately 187A in color is prominent along the edges of the three sepals and also on the three petals. A yellow patch 4B in color is found in the mid-section of the upper two petals.

Peduncle: Length, 4.4 cm.; color, green 138B.

Lasting quality: Good, approximately 14 days.

REPRODUCTIVE ORGANS

Stamens: Number, 6.

Anthers: Color, gray-brown 199C.

Filaments: Color, red-purple 63C.

Pistils: Number, 1; color red-purple 63C.

Stigma: Color, red-purple 63C.

I claim:

1. A new and distinct cultivar of Alstroemeria plant named Lorena, as illustrated and described.

* * * * *

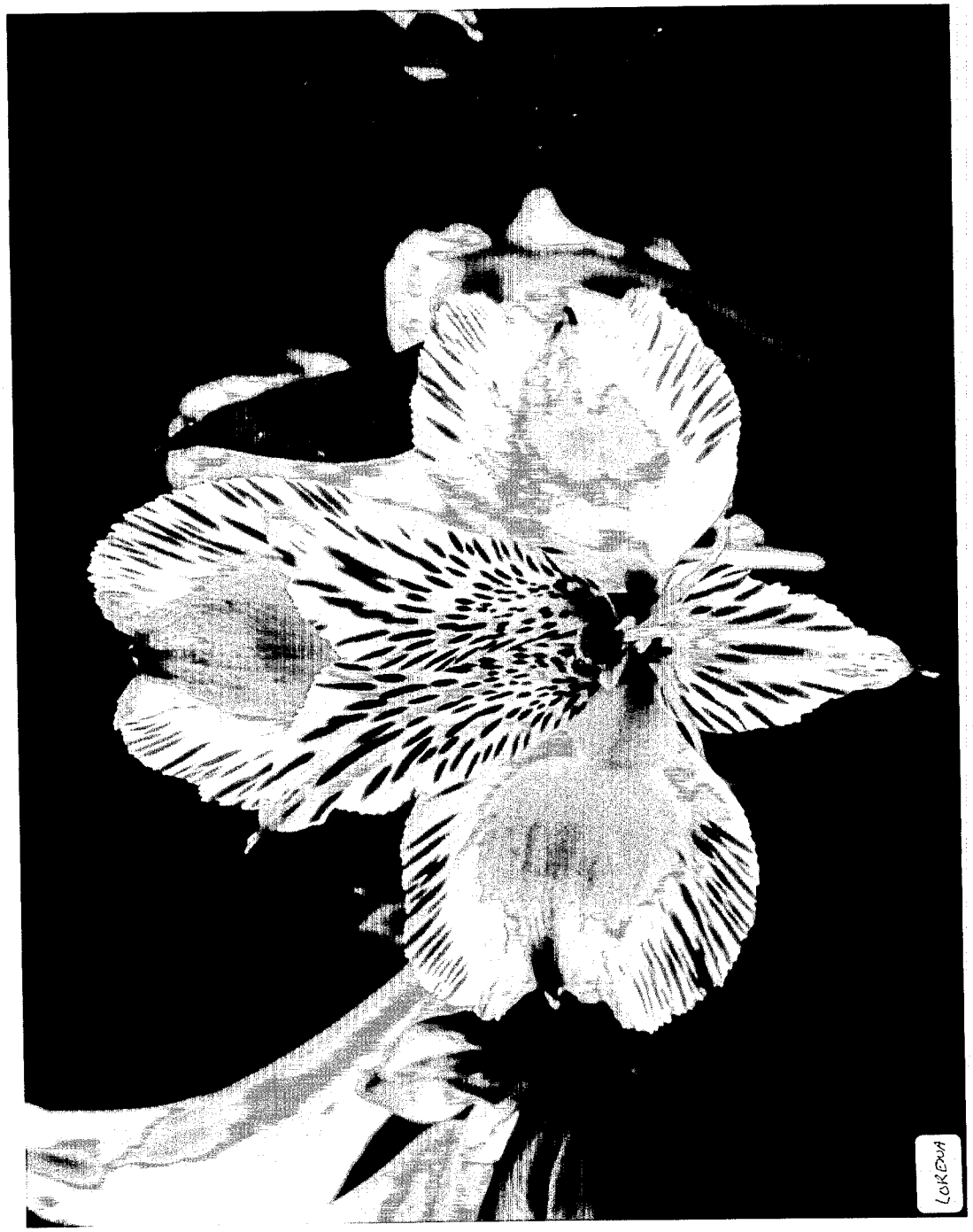
LOREXA